United States Patent [19]

Mendiratta

[11] Patent Number: 4,748,292

[45] Date of Patent: May 31, 1988

[54] METHOD FOR REMOVING POLYHALOGENATED HYDROCARBONS FROM NON-POLAR ORGANIC SOLVENT SOLUTIONS

[75] Inventor: Ashok K. Mendiratta, Schenectady, N.Y.

[73] Assignee: General Electric Company, Schenectady, N.Y.

[21] Appl. No.: 36,161

[22] Filed: Apr. 6, 1987

Related U.S. Application Data

[63] Continuation of Ser. No. 816,188, Jan. 6, 1986, abandoned.

[51] Int. Cl.$^4$ .............................................. C07C 33/34

[52] U.S. Cl. .................................... 585/469; 585/864; 585/868; 585/712; 208/262

[58] Field of Search ....................... 208/262, 180, 333; 585/469, 864, 868, 712; 210/909; 568/778

[56] References Cited

U.S. PATENT DOCUMENTS

| | | | |
|---|---|---|---|
| 4,022,795 | 5/1977 | Bamfield et al. | 260/590 R |
| 4,327,027 | 4/1982 | Howard et al. | 203/6 |
| 4,337,368 | 6/1982 | Pytlewski et al. | 568/730 |
| 4,351,718 | 9/1982 | Brunelle | 208/262 |
| 4,353,793 | 10/1982 | Brunelle | 208/262 |
| 4,400,552 | 8/1983 | Pytlewski et al. | 568/730 |

*Primary Examiner*—Helen M. S. Sneed
*Assistant Examiner*—Glenn Caldarola
*Attorney, Agent, or Firm*—Francis T. Coppa; James C. Davis, Jr.; James Magee, Jr.

[57] ABSTRACT

A method is provided for reducing the level of polychlorinated aromatic hydrocarbons dissolved in an organic solvent which avoids the accumulation of sticky residues on the equipment utilized.

3 Claims, No Drawings

METHOD FOR REMOVING POLYHALOGENATED HYDROCARBONS FROM NON-POLAR ORGANIC SOLVENT SOLUTIONS

This application is a continuation of application Ser. No. 816,188, filed Jan. 6, 1986, abandoned.

BACKGROUND OF THE INVENTION

Polychlorinated biphenyls, or "PCB's" were long used as dielectric fluids in electrical equipment because these materials have excellent heat stability, are non-flammable in nature, have low volatility and a good viscosity characteristic at operation temperatures. Because of their environmental persistence, however, continued manufacture, import or use in the United States was banned under the Toxic Substances Control Act of 1976, and the U.S. Environmental Protection Agency was directed to promulgate rules and regulations for their removal from the economy.

As of July 1, 1979, EPA regulations defined as "PCB-contaminated" any material containing more than 50 ppm of a mono-, di-, or polychlorinated biphenyl. The regulations permitted the disposal of PCB-contaminated materials by either incineration in an approved manner or in an approved landfill, but such procedures have rarely proven acceptable to community neighbors.

Since considerable fractions of the transformer oils, e.g., refined asphaltic-base mineral oil, or heat exchange oils, e.g., hydrogenated terphenyls, now in service are PCB-contaminated, the problem of disposing of PCB-contaminated hydrocarbon oils in an effective manner presents a serious challenge.

Various techniques for degrading the polyhalogenated hydrocarbons in such oils have been proposed. Most techniques are too lengthy and/or complex to provide a practical solution to the problem of PCB-contaminated oil. However, processes disclosed by Brunelle in U.S. Pat. Nos. 4,353,793, 4,351,718 and 4,410,422 provide rapid and effective degradation of PCB's in such oils. These processes utilize alkali metal hydroxides in combination with polyalkyleneglycols and/or monoalkyl ethers of polyethylene glycols. The above patents are assigned to the same assignee as the present invention and are incorporated herein by reference.

These reagents are insoluble in the contaminated transformer oil and are difficult to handle in conventional equipment. For example, the alkali metal hydroxide/glycol reagents and reaction products form a sticky viscous mass within the process equipment. This sticky viscous mass adheres to the surfaces of the process equipment such as the reactor chamber walls, filters, heat exchangers, conduits and valves. When neglected, this sticky mass will accumulate and can foul downstream equipment, such as filters, heat exchangers, etc. In addition, accumulation in the reactor reduces the heat transfer through the reactor walls. Such accumulation may require the process to be interrupted and the equipment cleansed by manually scraping and washing the same.

The present invention provides a method for removing polyhalogenated hydrocarbons from transformer oil without accumulation of the sticky viscous mass within the equipment utilized. The present invention is based on the discovery that the addition of small quantities of water upon completion of the reaction liberates the sticky viscous mass that adheres to the equipment surfaces.

STATEMENT OF THE INVENTION

There is provided by the present invention a method for treating a substantially inert, non-polar, organic solvent solution of polyhalogenated aromatic hydrocarbon which comprises (a) reacting the polyhalogenated aromatic hydrocarbon within said solution with a reagent comprised of an alkali metal hydroxide and a glycol selected from the group consisting of polyalkyleneglycol and monocapped polyalkyleneglycol alkyl ether to provide a reduced concentration of polyhalogenated aromatic hydrocarbon in said solution and (b) adding, with agitation, at least 0.25 wt % water to the reaction mixture of step (a).

An object of the present invention is to provide a faster and more efficient method for reducing the concentration of PCB's in transformer oil with a KOH and polyethylene glycol reagent.

Another object of the present invention is to provide a fast and efficient method for cleansing the equipment used to purify non-polar organic solvents, such as transformer oils.

Another object of the present invention is to improve the filtration of the transformer oils which are treated with KOH and polyethylene glycol reagents.

A further object of the present invention is to provide a method which permits easy separation of the reagents from the inert, non-polar organic solvent which is treated.

As indicated above, common inert organic solvent solutions which are PCB-contaminated are transformer oils. The term "transformer oil" signifies a mineral insulating oil of petroleum origin for use as an insulating and cooling media in electrical apparatus, for example, transformers, capacitors, underground cables, etc. These transformer oils are typically non-polar and inert.

The solutions which are treated preferably have a concentration of polyhalogenated aromatic hydrocarbon of up to 5% by weight based on the total weight of the reaction mixture. Higher concentrations of polyhalogenated aromatic hydrocarbon are difficult to handle.

The polyhalogenated aromatic hydrocarbon within the solution is typically the PCB's or polychlorinated biphenyls described above as mono-, di-, or polychlorinated biphenyl. Such compounds were commonly used in transformer oils for their unique properties, described more particularly above.

The alkali metal hydroxides which can be used to form the reagents are, for example, sodium hydroxide, potassium hydroxide, cesium hydroxide, etc. The concentration of such alkali metal hydroxides within the reaction mixture preferably ranges from about 0.1 to 10% by weight, as described more particularly by Brunelle in U.S. Pat. Nos. 4,351,718 and 4,353,793.

Where the glycol utilized to form the reagent is a polyalkyleneglycol, those which are preferred are, for example, polymers having a molecular weight in the range of from about 200 to 5000 including, for example, tetraethylene glycol, pentaethylene glycol, hexaethylene glycol, etc. The polyethylene glycols which are included can have molecular weights of, for example, 200, 300, 400, 600, 800, 1000, 1500, 3400, etc. The concentration of polyalkyleneglycol preferably ranges from about 0.1 to 10% by weight based on the total weight of the reaction mixture.

Where the glycol utilized is a monocapped polyalkyleneglycol alkyl ether, those which are preferred include polymers having a molecular weight in the range of from about 200 to 5000 and include, for example, polyethylene glycol monoethylethers having molecular weights in the range of 350 to 750, manufactured by the Aldrich Chemical Company of Milwaukee. Wis. The concentration of these monocapped polyalkyleneglycol alkyl ethers in the reaction mixture preferably ranges from about 0.1 to 10% by weight.

It has been found that a proportion of 1 to 50 equivalents of alkali metal of the alkali metal hydroxide, per OH of the polyalkyleneglycol or monocapped polyalkyleneglycol alkyl ether can be used to make the M'OH/PEG or M'OH/PEGM reagents, respectively. For the above formulas, M' represents an alkali metal as previously defined with respect to the alkali metal hydroxide usage, while PEG and PEGM represent the preferred polyalkyleneglycol, polyethylene glycol, and the preferred monocapped polyalkyleneglycol alkyl ether, monocapped polyethylene glycol methylether, respectively.

It has been found that at least one equivalent of alkali metal per OH of the PEG or PEGM will remove one equivalent of halogen atom from the PCB. Higher amounts are preferred to facilitate PCB removal.

The reagents described above can be preformed, or the aforementioned ingredients can be added separately within the limits described above to a non-polar organic solvent to form the reagents within the reaction mixture. Experience has shown that agitation of the resulting mixture, such as stirring or shaking is necessary to achieve effective results.

To effectively monitor the reduction or removal of PCB or polyhalogenated aromatic hydrocarbon contamination, such as polychlorinated biphenyl contamination in a nonpolar, inert organic solvent, a vapor phase chromatograph (VPC), for example Model No. 3700, of the Varian Instrument Company, can be used in accordance with the following procedure: An internal standard, for example, n-docosane can be added to the initial reaction mixture. The standard is then integrated relative to the PCB envelope to determine ppm concentration upon VPC analysis.

Temperatures in the range of 90° C. to 120° C. are preferred for reducing the level of the polyhalogenated hydrocarbons with the reagents described above, whereas a temperature in the range of 65° C. to 200° C. can be used.

To effectively remove the sticky viscous mass from the equipment surfaces, the concentration of water added to the reaction mixture must be greater than 0.25% by weight based on the total reaction mixture. In that water poisons the reaction, addition of such water must be accomplished upon completion of the removal of the polyhalogenated hydrocarbons. It is preferable to add water when the concentration of polyhalogenated hydrocarbons falls below 2 ppm so that the solution is no longer a "PCB-contaminated material" as defined by the EPA. Furthermore, it is preferable to add a quantity of water sufficient to provide from 0.5% to 10% by weight water, and most preferable 0.5% to 2% by weight water, based on the total reaction mixture. High concentrations of water within these ranges may dissolve all of the solids within the reaction mixture. This will simplify handling and separation of the reagents from the treated inert organic solvent. Filtration of the reaction mixture may be avoided and the reagents simply decanted from the treated inert organic solvent.

Where filtration is still desired, the filtration step will be accelerated due to the absence of the sticky viscous mass. In addition, the process of this invention is particularly useful in cleansing the reactor vessel. The addition of water will liberate the sticky viscous mass which accumulates on the surfaces of the reactor.

Concentrations of water beyond the preferred range given above (10% by weight) will achieve the desired objects of this invention; however, these large quantities of water are unnecessary.

In order that those skilled in the art will be better able to practice the present invention, the following examples are given by way of illustration and are not intended to limit the scope of this invention to the embodiments described. All parts are by weight unless otherwise indicated.

EXAMPLE 1

This example illustrates prior art processes and is provided for the purpose of comparing filtration time with Example II.

Transformer oil (1600 gms) contaminated with polychlorinated biphenyls (500 ppm PCB's) was poured into a reaction vessel and heated to 98° by injecting steam into the vessel's jacket. This was followed by the addition of potassium hydroxide (20 gms) and monocapped polyethylene glycol methylether (20 gms). The potassium hydroxide used was 85% pure and ground to a powder. The monocapped polyethylene glycol methylether had an average molecular weight of about 350. The reactor contents were maintained at 98° C. with efficient stirring. Reaction was carried on for about 15 minutes following which, the reactor was drained. A coating of solids was observed on the reactor wall, which could not be easily removed and the reactor contents had a jelly/solid suspended phase. The reactor contents were then cooled and filtered through a medium size fritted funnel (with vacuum). Filtration took approximately 4 hours. The PCB content of the resulting oil was less than 1 part per million and 1510 gms of oil were recovered.

EXAMPLE 2

Example 1 was repeated except that 10 gms of water were added to the reaction vessel following completion of the reaction. The reactor contents were allowed to mix for 4 minutes and the reactor was drained. The reactor contents were cooled and filtered through a medium size fritted funnel (with vacuum). Filtration took approximately 20 minutes. The PCB content of the resulting oil was less than 1 part per million and 1590 gms of oil were recovered from this process. Furthermore, the reactor walls did not contain a coating of solids.

EXAMPLE 3

Example 1 was repeated except that 20 gms of water were added to the reaction vessel following the completion of the reaction. The reactor contents were allowed to mix for 4 minutes and the reactor was drained. No solids were observed in the reactor contents which comprised two distinct liquid phases, an aqueous polar phase and a non-polar organic phase, which were amenable to separation by decantation.

Obvious modifications of the above embodiments are considered to be within the scope of this invention.

What is claimed is:

1. In a method for reducing the concentration of polyhalogenated aromatic hydrocarbons present in a non-polar inert organic solvent solution comprising reacting in a reactor the polyhalogenated aromatic hydrocarbon with a reagent comprising an alkali metal hydroxide and a glycol selected from the group consisting of polyalkylene glycol and monocapped polyalkylene glycol ether, the improvement comprising maintaining the reaction mixture under substantially water-free conditions until the concentration of polyhalogentated aromatic hydrocarbons has been reduced below about 2 ppm, and then adding to the reaction mixture at least about 0.25% by weight water, whereby sticky viscous solids are removed from the reactor.

2. The method of claim 1 wherein the reactor surfaces are cleaned of sticky viscous solids.

3. The improvement of claim 1 wherein the amount of water added to the reaction mixture is from about 0.5% to about 10% by weight, based on the total reaction mixture.

* * * * *